(12) United States Patent
Pyun

(10) Patent No.: US 11,624,745 B2
(45) Date of Patent: Apr. 11, 2023

(54) METHOD OF SCREENING ANTIBODY AND ANTIBODY SCREENING SYSTEM USING THE SAME

(71) Applicant: UNIVERSITY-INDUSTRY FOUNDATION(UIF), YONSEI UNIVER, Seoul (KR)

(72) Inventor: Jae-Chul Pyun, Seoul (KR)

(73) Assignee: UNIVERSITY-INDUSTRY FOUNDATION (UIF), YONSEI UNIVERSITY, Seoul (KR)

(*) Notice: Subject to any disclaimer, the term of this patent is extended or adjusted under 35 U.S.C. 154(b) by 160 days.

(21) Appl. No.: 16/805,825

(22) Filed: Mar. 1, 2020

(65) Prior Publication Data

US 2020/0371092 A1 Nov. 26, 2020

(51) Int. Cl.
*G01N 33/537* (2006.01)
*G01N 33/577* (2006.01)
*G01N 33/554* (2006.01)

(52) U.S. Cl.
CPC .......... *G01N 33/537* (2013.01); *G01N 33/554* (2013.01); *G01N 33/577* (2013.01)

(58) Field of Classification Search
CPC .................. A61K 39/00; A61K 39/395; A61K 39/39525; G01N 33/6854; G01N 33/577; G01N 33/554; G01N 33/537; G01N 2500/04

USPC .......... 424/130.1, 141.1, 150.1, 151.1, 152.1, 424/159.1, 164.1, 178.1
See application file for complete search history.

(56) References Cited

PUBLICATIONS

Korean Office Action dated Jun. 11, 2020; Application No. 10-2019-0059783.
Ji-Hong Bong et al., 'Fluorescence immunoassay of *E. coli* using anti-lipopolysaccharide antibodies isolated from human serum', Biosensors and Bioelectronics, (Nov. 2018), vol. 126, pp. 518-528.

*Primary Examiner* — Jana A Hines
(74) *Attorney, Agent, or Firm* — McLean IP Global; Jason Y. Pahng

(57) ABSTRACT

A method of screening an antibody comprises preparing a serum having a target antibody and a non-target antibody; providing the serum with a first antigen that specifically binds the target antibody to obtain a first mixture; selectively obtaining the first conjugate by separating the first conjugate from the non-target antibody in the first mixture; dissociating the first conjugate, and a redundant non-target antibody adsorbed to the first conjugate into the first antigen, the target antibody and the redundant non-target antibody; removing the first antigen to obtain a second mixture of the target antibody and the redundant non-target antibody; providing the second mixture with a second antigen to form a second conjugate, so that third mixture including the target antibody and the second conjugate may be obtained; and selectively obtaining a target antibody by separating the second conjugate from the target antibody in the third mixture.

10 Claims, 5 Drawing Sheets

METHOD OF SCREENING ANTIBODY AND ANTIBODY SCREENING SYSTEM USING THE SAME

CROSS-REFERENCES TO RELATED APPLICATION

The present application claims priority under 35 U. S. C. 119(a) to the Korean application number 10-2019-0059783 filed on May 22, 2019, which is herein incorporated by reference in its entirety.

BACKGROUND OF THE INVENTION

1. Field

The present invention relates to a biomaterial detection technology, and more particularly, to an antibody screening method and an antibody screening system using the same.

2. Description of the Related Art

The immune system produces antibodies to protect the body from inflammation caused by viruses, bacteria or contamination and to eliminate the cause of the disease. The antibody may perform the defense function of the immune system by neutralizing or eliminating the antigen through an antigen-antibody reaction that specifically binds to the target antigen. Recently, therapeutic methods for removing toxins, proteins, viruses, parasites or cells using the antigen-antibody response have been developed, which are called passive immunotherapy or passive serum therapy.

In conventional passive serum therapy, a target antigen is injected into the animal's immune system for the production of the antibody to activate the humoral immune system and allow B cells of the immune system to produce the antibody. By the way, when the antigen is injected into the body of the animal to adversely affect the physiological activity of the animal or the activity of the immune system, the activity of the immune system is reduced and the production of antibodies is difficult. In addition, due to the recent emergence of a number of causes of diseases, it is urgent to develop an efficient and economical method for producing antibodies due to considerable cost and time for producing antibodies specific for the diseases.

In addition, when the antibody is produced using an animal's immune system, it is important to select an antibody that selectively responds to a target disease. In the humoral immune system, antigens are differentiated into several pieces of epitopes by antigen presenting cells, and they produce antibodies that specifically respond to each epitope when B cells are differentiated by the different types of epitopes. Antibodies that respond to one epitope are called monoclonal antibodies (Mab), and polyclonal antibodies that contain a mixture of antibodies that respond to different epitopes. Therefore, the serum therapy may require a screening process of an antibody that selectively reacts with a target antigen among the various kinds of antibodies.

SUMMARY OF THE INVENTION

The technological problem to be achieved by the present invention is to provide an antibody screening method capable of producing an effective amount of an antibody by producing and screening antibodies outside the body according to a method that does not directly inject the antigen into the immune system of the target animal or human body without involving the physiological activity of the animal or human body or changes in the immune system.

Another technological problem to be achieved by the present invention is to provide an antibody screening system for producing and screening antibodies specific to a target disease at low cost and time.

A method of screening an antibody according to an embodiment for solving the above problems may comprise a step for preparing a serum having a target antibody and a non-target antibody from a subject; a step for providing the serum with a first antigen that specifically binds the target antibody to obtain a first mixture comprising the target antibody, the first conjugate of the first antigen, and the non-target antibody; a step for selectively obtaining the first conjugate by separating the first conjugate from the non-target antibody in the first mixture; a step for dissociating the first conjugate, and a redundant non-target antibody adsorbed to the first conjugate into the first antigen, the target antibody and the redundant non-target antibody; a step for removing the first antigen to obtain a second mixture of the target antibody and the redundant non-target antibody; a step for providing the second mixture with a second antigen that specifically binds the redundant non-target antibody to form a second conjugate consisting of the redundant non-target antibody and the second antigen, so that third mixture including the target antibody and the second conjugate may be obtained; and a step for selectively obtaining a target antibody by separating the second conjugate from the target antibody in the third mixture. In another embodiment, the concentration of the first antigen in the step for obtaining the first mixture may be in the range of $10^6$ cells/ml to $10^8$ cells/ml, and in another embodiment, the concentration of the second antigen may be in the range of $10^6$ cells/ml to $10^8$ cells/ml in the step for obtaining the third mixture.

In one embodiment, when the first antigen AG1 is an LTA antigen including LTA (lipoteichoic acid) in at least some portions of the first antigen AG1, the second antigen AG2 may be an LPS antigen including LPS (lipopolysaccharide) in at least some portions of the second antigen AG2. When the first antigen AG1 is an LPS antigen including LPS in at least some portions of the first antigen AG1, the second antigen AG2 may be an LTA antigen including LTA in at least some portions of the second antigen AG2. In another embodiment, the LTA antigen may comprise Gram positive bacteria, and in another embodiment, the LPS antigen may comprise Gram negative bacteria.

In one embodiment, the LTA antigen may include at least any one or more of taphylococcus, streptococcus, pneumococcus, leprosy, *M. leprae, C. diphtheriae, C. tetani, B anthracis*, actinobacteria or *B. subtilis*. In another embodiment, the LPS antigen may include at least any one or more of *Klebsiella penumoniae, Acinetobacter baumannii, Pseudomonas aeruginosa, Enterobacter* spp., *Salmonella, shigella, R. rickettsii, E. coli, V. cholerae, Y. pestis, N. gonorrhoeae, N. meningitidis* or *spirochaeta*.

In one embodiment, the step for obtaining the first mixture may further comprise a step for providing an environment for an immune response based on the first antigen in the serum to produce the target and non-target antibodies. In another embodiment, the first conjugate may be dissociated into the first antigen, or the second antigen and the first antigen when an acid solution is provided. In another embodiment, the antibody screening method may repeat at least more than two times the step for obtaining the third mixture and the step for selectively obtaining the target antibody.

In one embodiment, the antibody screening method may further comprise the step for extracting the target antibody from a mixed solution comprising the target antibody separated from the second conjugate. In another embodiment, the step for extracting the target antibody may use at least one or more of ion exchange chromatography, hydrophobic interaction chromatography (HIC), protein-G chromatography, or protein-A chromatography.

An antibody screening system according to an embodiment for solving the above problems may comprise a first container for obtaining a first mixture including a first conjugate consisting of a target antibody and a first antigen, and a non-target antibody by preparing serum having the target antibody and the non-target antibody from a subject, and providing the serum with the first antigen that specifically binds the target antibody; a first separator for separating the first conjugate and the non-target antibody in the first mixture to selectively obtain the first conjugate; a second container for dissociating the first conjugate, and the redundant non-target antibody adsorbed to the first conjugate into the first antigen, the target antibody and the redundant non-target antibody; a second separator for obtaining a second mixture of the target antibody and the redundant non-target antibody by removing the first antigen; a third container for obtaining a third mixture consisting of the target antibody and a second conjugate by providing a second antigen that specifically binds the redundant non-target antibody to the first mixture and forming the second conjugate consisting of the redundant non-target antibody and the second antigen; and a third separator for selectively obtain a target antibody by separating the second conjugate and the target antibody from the third mixture. In another embodiment, the first container may provide an environment for an immune response based on the first antigen in the serum to produce the target and non-target antibodies. In another embodiment, the antibody screening system may further include a purification unit for purifying the target antibody from the mixed solution from which the second conjugate has been removed.

In one embodiment, the purification unit may use at least one or more of ion exchange chromatography, hydrophobic interaction chromatography (HIC), protein-G chromatography or protein-A chromatography. In another embodiment, the first conjugate may be dissociated into the first antigen or the second antigen and the first antigen when an acid solution is provided. In yet another embodiment, when the first antigen AG1 is an LTA antigen including LTA (lipoteichoic acid) in at least some portions of the first antigen AG1, the second antigen AG2 may be an LPS antigen including LPS (lipopolysaccharide) in at least some portions of the second antigen AG2. When the first antigen AG1 is an LPS antigen including LPS in at least some portions of the first antigen AG1, the second antigen AG2 may be an LTA antigen including LTA in at least some portions of the second antigen AG21.

In one embodiment, the LTA antigen may include Gram-positive bacteria, and in another embodiment, the LPS antigen may include Gram-negative bacteria. In yet another embodiment, LTA antigen may include at least any one or more of streptococcus, pneumococcus, leprosy, *M. leprae*, *C. diphtheriae*, *C. tetani*, *B anthracis*, actinobacteria or *B. subtilis*. In yet another embodiment, the LPS antigen may include *Klebsiella penumoniae*, *Acinetobacter baumannii*, *Pseudomonas aeruginosa*, *Enterobacter* spp., *Salmonella*, *shigella*, *R. rickettsii*, *E. coli*, *V. cholerae*, *Y. pestis*, *N. gonorrhoeae*, *N. meningitidis* or *spirochaeta*.

According to an embodiment of the present invention, Gram-positive bacteria and Gram-positive bacteria are used for screening antibodies specifically binding to lipoteichoic acid (LTA), a constituent of Gram-positive bacteria, and lipopolysaccharide (LPS), a constituent of Gram-negative bacteria. Therefore, unlike the case directly injecting the lysophosphatidic acid or the lipopolysaccharide into an animal, an antibody selection kit capable of producing an antibody without accompanying a change in physiological activity may be provided.

According to another embodiment of the present invention, it is possible to provide an antibody screening method and the method which may be carried out at low cost without performing complicated processes by using an antigen-antibody reaction by the Gram-positive bacteria and the Gram-negative bacteria.

DETAILED DESCRIPTION OF THE INVENTION

Figure 1:
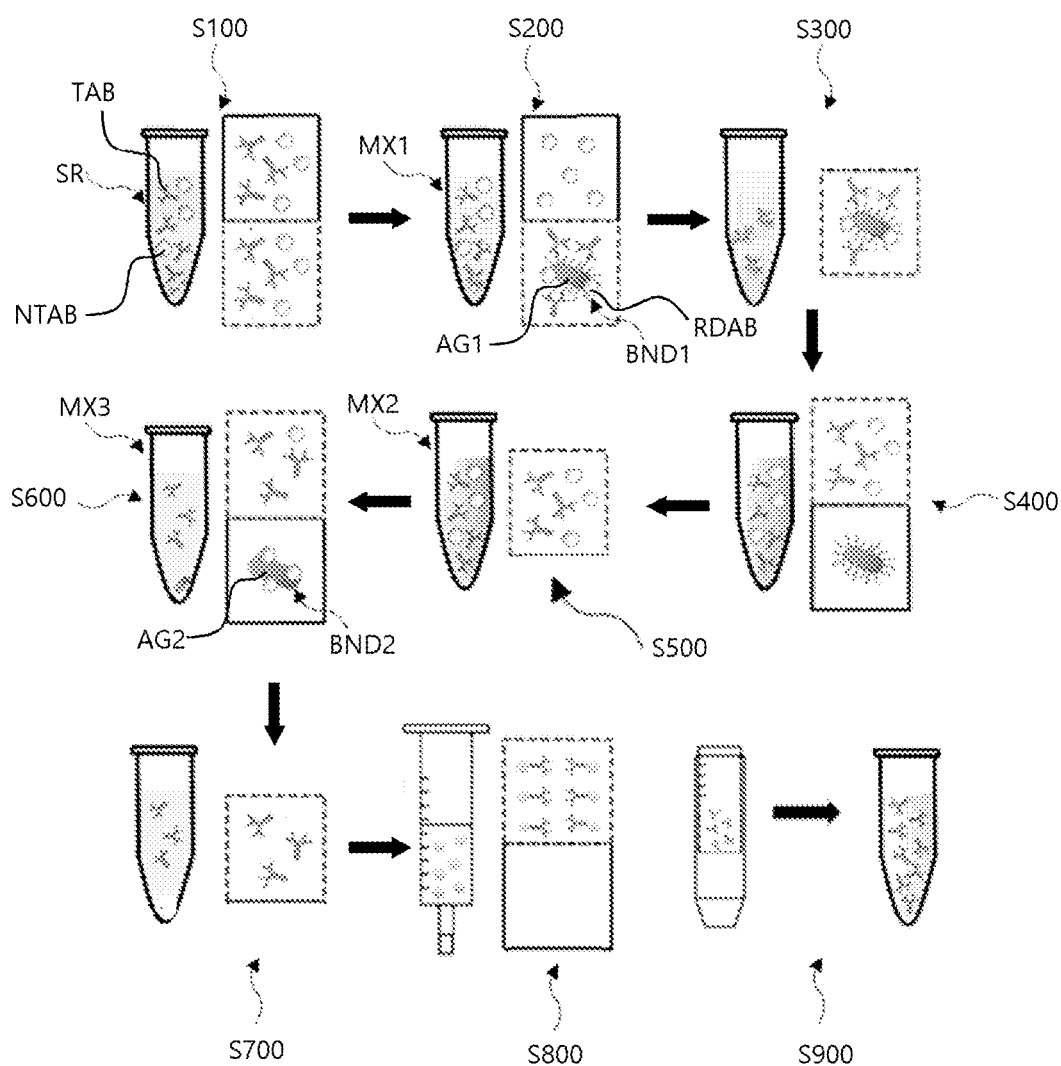
FIG. 1 is a flow chart of an antibody screening method according to an embodiment of the present invention, where the reference numerals S100 to S900 denote steps, SR denotes serum, TAB denotes a target antibody, NTAB denotes a non-target antibody, MX1 denotes a first mixture, AG1 denotes a first antigen, BND1 denotes a first conjugate, RDAB denotes a redundant non-target antibody, MX2 denotes a second mixture, MX3 denotes a third mixture, AG2 denotes a second antigen, and BND2 denotes a second conjugate.

Hereinafter, the preferred embodiments of the present invention will be described in detail with reference to the accompanying drawings.

The embodiments of the present invention are provided to more fully explain the present invention to those skilled in the art. The following embodiments may be modified in many different forms and the scope of the invention should not be construed as being limited to the following embodiments. Rather, these embodiments are provided so that this disclosure may be explained more faithfully and completely, and the concepts of the invention may be fully conveyed to those skilled in the art.

In the drawings, the same reference numerals refer to the same elements. In addition, as used herein, the term "and/or" includes any one of the listed items, and all combinations of one or more of the listed items.

The terms used herein is for the purpose of describing particular embodiments only and is not intended to be limiting the scope of the invention. In addition, although described in the singular in this specification, a plural form may be included unless the singular in the context clearly indicates. Also, as used herein, the terms, "comprise" and/or "comprising" specify the shapes, numbers, steps, operations, members, elements and/or, addition or presence of these groups which are mentioned in foregoing paragraphs. It does not exclude the presence or addition of other shapes, numbers, operations, members, elements and/or, addition or presence of these groups.

The reference herein to a layer formed "on" a substrate or other layer refers to a layer formed directly on or above the substrate or other layer, or formed on an intermediate layer or intermediate layers formed on the substrate or other layer. Also, it is apparent to those skilled in the art that a structure or shape disposed "adjacent" to another shape may have portions that overlap or are disposed below the adjacent shape.

In this specification, the relative terms such as "below", "above", "upper", "lower", "horizontal" or "vertical" may be used to describe the relationship between a component member, a layer or a region and another component member, layer or region, as shown in the drawings. It is to be understood that these terms encompass not only the directions indicated in the drawings, but also other directions of the device.

In the following specification, the embodiments of the present invention will be described with reference to cross-sectional views schematically showing ideal embodiment (and intermediate structures) of the present invention. In these drawings, for example, the size and shape of the members may be exaggerated for convenience and clarity of description, and in actual implementation, variations of the illustrated shape may be expected. Accordingly, embodiments of the invention should not be construed as being limited to the specific shapes of the regions shown herein. Also, reference numerals of members in the drawings refer to the same members throughout the drawings.

The term "antibody" may include antibodies, antibody derivatives or fragments thereof, and the detailed description of the antibodies also applies to the antibody selection methods of the present invention. The antibody includes the equivalent of the antibody, such as polypeptide among the fragments, or the antibody homologues includes an Fc region, an immunoglobulin binding domain, a peptide that mimics the binding domain, a region homologous to the Fc region, or at least a portion thereof.

In addition, the antibody may comprise a chimeric molecule comprising an immunoglobulin binding domain fused to another polypeptide or equivalent thereof. The antibodies may be intact immunoglobulin molecules, and may include the components of the antibody such as Fab, Fab ', F(ab')2, Fc and F(v), N-glycan structures and paratopes, and may also include at least some of the components.

The antibody is a basic component of serum and may be a collection of the antibodies, immunoglobulin molecules or fragments thereof, and may be a single molecule of an antibody or immunoglobulin. The antibody molecule may induce an immunological effector mechanism by binding to or reacting with a specific antigenic determinant such as an antigen or epitope of the antigen. The antibody may be monospecific, and the composition of the antibodies may be monoclonal consisting of the same antibodies, and it may be polyclonal including other epitopes of the same antigen or other types of antibodies that react with epitopes of different antigens. Each antibody has a unique structure that allows for specific binding of the antibody to the corresponding antigen and all natural antibody molecules may have the identical basic structure such as two identical light chains and two identical heavy chains as a whole.

FIG. 1 is a flow chart of an antibody screening method according to an embodiment of the present invention. For convenience of description, the subject performing the steps included in the antibody screening method may be omitted.

Referring to FIG. 1, in one embodiment, serum SR having a target antibody TAB and a non-target antibody NTAB extracted from a subject is prepared (S100). The subject may be a mammal, such as a rabbit, goat, or pig, or may be a human body. In another embodiment, the subject may be a corpse of an animal which is dead due to a disease of the animal or a subject antigen. For example, when the target antibody TAB is used as a means for treating a human disease, it may be preferable to use serum SR extracted from the human body in consideration of compatibility with the human body. According to one embodiment of the invention, the production of the target antibody TAB by using the serum SR extracted from the subject is produced in vitro. Therefore, unlike production in vivo, it is possible to produce and select antibodies which do not involve changes in the subject's immune system or physiological activity.

In one embodiment, serum SR may be provided to a cell pellet. In other embodiments, it may include all kinds of containers such as a plurality of wells, cells, substrates or plates, including materials such as glass, plastics, polymers. However, this is exemplary and all containers capable of providing a reaction region of an antibody, antigen or serum SR may be applicable and are not limited to specific examples.

Thereafter, a first antigen AG1 that specifically binds to the target antibody TAB is provided to the serum SR, and a first mixture MX1 including the first conjugate BND1 of the target antibody TAB and the first antigen AG1, and the non-target antibody NTAB may be obtained (S200). In one embodiment, the first antibody may be an LTA antigen in which LTA is contained in at least some parts, and the target antibody TAB may be an LTA antibody. In another embodiment, the first antibody may be LPS antigen in which LPS antigen is contained in at least some parts, and the target antibody TAB may be an LPS antibody.

Since the first antigen AG1 has a specific reactivity with the target antibody TAB, the first conjugate BND1 is composed of the target antibody TAB coupled with the first antigen AG1. Further, since the non-target antibody NTAB is chemically, electrically or physically adsorbed to the first antigen AG1, a redundant non-target antibody RDAB may intervene as an impurity in the first conjugate BND1. The amount of redundant non-target antibody RDAB may vary depending on the type and composition of the first antigen AG1, target antibody TAB or non-target antibody NTAB, the concentration of the aforementioned substances, or the reactivity with the solvent. The amount of redundant non-target antibody RDAB may be less than the amount of target antibody TAB specifically bound to the first antigen AG1. In the present specification, the provision of the first antigen AG1 means that the first antigen AG1 and the serum SR are mixed, and the manner in which the first antigen AG1 is mixed is not limited to a specific manner.

In another embodiment, the concentration of the first antigen AG1 in step S200 for obtaining the first mixture MX1 may be determined in consideration of the amount of target antibody TAB to be obtained. When the concentration of the first antigen AG1 is lower than the amount of the target antibody TAB, since the amount of the first conjugate BND1 bound to the target antibody TAB, and the first antigen AG1 contained in the serum SR is not sufficient, acquisition rate of antibody screening is degraded. On the contrary, if the concentration of the first antigen AG1 is higher compared to the amount of the target antibody TAB, an unnecessarily large amount of the first antigen AG1 should be used, and the amount of the redundant non-target antibody RDAB is increased. Therefore, the steps (S600, S700) to remove redundant non-target antibody RDAB should be performed additionally.

In one embodiment, in order to efficiently form the first conjugate BND1, the concentration of the first antigen AG1 may be in the range of $10^6$ cells/ml to $10^8$ cells/ml. Preferably, the concentration of the first antigen AG1 is $10^7$ cells/ml before a mixing process, and the first antigen AG1 and the antibody may be mixed in a volume ratio of 1:1.

In another embodiment, the step S200 for obtaining the first mixture MX1 provides an environment for the immune response based on the first antigen AG1 of serum SR and thus, it may further comprise the step for generating target antibody TAB and non-target antibody NTAB. The humoral immune system of an animal may produce antibodies by using B cells, which may have $10^9$ to $10^{11}$ clones. The B cells may also produce antibodies against various types of antigens, such as the constituents of the bacterial outer membrane.

For example, lipopolysaccharide (LPS) or lipoteichoic acid (LTA) may be present as the outer membrane constituent of the bacterium, and a detailed description thereof will be described later. Accordingly, in one embodiment, B cells may differentiate into target antibody TAB and non-target antibody NTAB when a first antigen AG1 is provided to serum (SR) to generate an immune response. For example, a mixed solution containing the first antigen AG1 and the serum SR may be incubated at 25° C. for 1 hour.

Thereafter, the first conjugate BND1 and the non-target antibody NTAB may be separated from the first mixture MX1 to selectively obtain the first conjugate BND1 (S300). In an exemplary embodiment, the first mixture BND1 may be deposited by centrifugation of the first mixture MX1 to separate the first conjugate BND1 from the non-target antibody NTAB. For example, the first mixture BND1 may be precipitated by gravity by leaving the first mixture MX1. In order to separate the precipitated first binder BND1, the mixed solution remaining on the first binder BND1 may be removed, and the precipitated first binder BND1 may be extracted. In another embodiment, a process using manure, distillation, density difference, centrifuge, spinning band extraction, Pulsating Sieve Tray or Packed Columns Extraction Systems or a liquid mixer-settler method may be used. Alternatively, protein chromatography may be used to remove the upper non-target antibody NTAB. The aforementioned centrifugation or chromatography is exemplary, and various other known techniques including the magnetic force, the electrical force, or solubility for separating the first conjugate BND1 and non-target antibody NTAB from the first mixture MX1 may be used.

Thereafter, the first conjugate BND1, and the redundant non-target antibody RDAB adsorbed on the first conjugate BND1 may be separated into the first antigen AG1, the target antibody TAB and the redundant non-target antibody RDAB (S400). In one embodiment, the first conjugate BND1 and the redundant non-target antibody RDAB may be treated with the acid solution. For example, glycine-HCl buffer (pH 2.7, 0.1M) may be used. In other embodiments, compounds such as sodium chloride (NaCl) or magnesium chloride ($MgCl_2$), urea, or guanidinium salts may be used. The pH and concentration of the aforementioned materials may be appropriately adjusted according to factors such as the type of antigen-antibody, binding property, reaction conditions.

Thereafter, the first antigen AG1 may be removed to obtain a second mixture MX2 consisting of the target antibody TAB and the redundant non-target antibody RDAB (S500). The mixed antigen containing the dissociated first conjugate BND1 and the redundant non-target antibody RDAB is centrifuged at a rotational speed of 10,000 rpm to 15,000 rpm, preferably 11,000 rpm to precipitate the first antigen AG1. Thereafter, the precipitated first antigen AG1 may be removed to obtain a second mixture MX2 including a target antibody TAB and a redundant non-target antibody RDAB that remain on top without being precipitated. In another embodiment, the second mixture MX2 remaining at the top may be extracted using experimental tools such as pipettes and spoids.

Thereafter, the second mixture MX2 is provided with a second antigen AG2 that specifically binds to the redundant non-target antibody RDAB, and thus, second conjugate BND2 of the redundant non-target antibody RDAB and the second antigen AG2 may be formed to obtain a third mixture MX3 containing the target antibody TAB and the second conjugate BND2 (S600). This is the process for completely removing a redundant non-target antibody RDAB in which a portion of the non-target antibody NTAB is adsorbed to the first antibody and remains in the mixed solution during the steps (S100 to S500) for filtering out the non-target antibody NTAB using the first antigen AG1. The second antigen AG2 may form a second conjugate BND2 via the antigen-antibody reaction with the non-target antibody NTAB. In one embodiment, where the first antigen AG1 is an LTA antigen, the second antigen AG2 may be an LPS antigen and the non-target antibody NTAB may be an LPS antigen. On the contrary, in another embodiment, when the antigen AG1 is an LPS antigen, the second antigen AG2 may be an LTA antigen and the non-target antibody NTAB may be an LTA antigen.

In one embodiment, an incubation process may be performed as described above to facilitate the reaction of the second antigen AG2 with the non-target antibody NTAB. The incubation process may be performed at 25° C. for about 1 hour, for example.

Thereafter, the second conjugate BND2 and the target antibody TAB may be separated from the third mixture MX3 to selectively obtain the target antibody TAB (S700). In order to obtain a target antibody TAB, the second conjugate BND2 may be removed from the mixed solution, or the portion containing the target antibody TAB may be selectively selected from the mixed solution. As a method for separating the second conjugate BND2 and the target antibody TAB, the step (S300) for selectively obtaining the first conjugate BND1 by separating the first conjugate BND1 and the non-target antibody NTAB (S300) may be referred to.

In one embodiment, the concentration of the second antigen AG2 may be appropriately adjusted to obtain high selectivity and yield, so that redundant non-target antibody RDAB may be removed, which means that the adjustment of the concentration may be changed based on type, reactivity or experimental conditions of at least one of the target antibody TAB, non-target antibody NTAB, or second antigen AG2. When the concentration of the second antigen AG2 is lower than the concentration of the antibodies, all of the redundant non-target antibody RDAB are not removed and remain as they are, and the second antigen AG2 is provided to form the second conjugate BND2 (S600). In addition, it is required to repeat the step (S700) for selectively obtaining the target antibody TAB by separating the second conjugate BND2 and the process should be performed additionally. In addition, when the concentration of the second antigen AG2 is higher than that of the antibodies, the target antibody TAB may be partially adsorbed to the second antigen AG2, thereby lowering the yield of antibody screening. In another embodiment, the concentration may be in the range of $10^6$ cells/ml to $10^8$ cells/ml, preferably $10^7$ cells/ml. The volume ratio of the solution including the third mixture MX3 and the second antigen AG2 may be 1:1. In various embodiments, the concentration of the second antigen AG2, and the volume ratio of the solution including the second antigen AG2 and the third mixture MX3 may be appropriately adjusted according to the type of the second antigen AG2, the type of the non-target antibody NTAB, the type of the target antibody TAB and scale of mutual reactivity of afore-mentioned substances.

In one embodiment, the antibody screening method may repeat the step (S600) for obtaining the third mixture MX3 and the step (S700) for selectively obtaining the target antibody TAB at least two or more times. By repeating the steps (S600, S700), the redundant non-target antibody RDAB mixed with the target antibody TAB may be removed, so that the target antibody TAB in which non-target antibody NTAB does not remain may be optionally obtained with high yield. In one embodiment, the steps (S600, S700) may be repeated twice, and may be repeated more times to increase the yield of the target antibody TAB.

In another embodiment, the antibody screening method may further comprise a step (S800) for purifying the first antibody from the mixed solution from which the second binder BND2 has been removed. For example, at least one or more of ion exchange chromatography, hydrophobic interaction chromatography (HIC), protein-G chromatography, or protein-A chromatography may be used. Protein A is a cell surface protein found in *Staphylococcus aureus*. It has the property of binding to the Fc region of mammalian antibodies, in particular IgG class antibodies. In another embodiment, the method may further include a step (S900) for eluting with a solvent and then concentrating after separation using protein-A chromatography. The use of the method for the purification of antibodies, in particular monoclonal IgG, is described in detail in the known art. For example, Langone et al., Supra; 1972 edition of FEBS Lett, co-authored by Hjelm et al. 28, pp. 73-76, which is hereby incorporated by reference in its entirety.

In one embodiment, when the first antigen AG1 is an LTA antigen including LTA (lipoteichoic acid) in at least some portions of the first antigen AG1, the second antigen AG2 may be an LPS antigen including LPS (lipopolysaccharide) in at least some portions of the second antigen AG2. When the first antigen AG1 is an LPS antigen including LPS in at least some portions of the first antigen AG1, the second antigen AG2 may be an LTA antigen including LTA in at least some portions of the second antigen AG21.

For example, when the target antibody TAB is an LTA antibody, the non-target antibody NTAB may be an LPS antibody. On the contrary, when the target antibody TAB is an LPS antibody, the non-target antibody NTAB may be an LTA antibody. The LTA and the LPS are oligosaccharides present in the cell wall of bacteria. When bacteria including the LTA and the LPS are introduced into the body to cause an infection, fever may occur due to the LTA and the LPS, leading to death. Conventionally, in order to separate the antibody against the LTA and the antigen against the LPS, an affinity chromatography immobilized the LTA antigen or the LPS antigen has been used, but it was difficult to commercialize because of low efficiency. The present invention provides a solution process, in which the LTA antigen and the LPS antigen are injected directly into serum SR without immobilization to cause an antigen-antibody reaction. Therefore, highly efficient selection of the LTA antibody and LPS antibody is possible.

In another embodiment, the LTA antigen may include Gram-positive bacteria, and for example, may include at least any one or more of *streptococcus*, pneumococcus, leprosy, *M. leprae*, *C. diphtheriae*, *C. tetani*, *B anthracis*, actinobacteria or *B. subtilis*. In another embodiment, the LPS antigen may include Gram-negative bacteria, and for example, may be *Klebsiella* penumoniae, *Acinetobacter baumannii*, *Pseudomonas aeruginosa*, *Enterobacter* spp., *Salmonella*, *shigella*, *R. rickettsii*, *E. coli*, *V. cholerae*, *Y. pestis*, *N. gonorrhoeae*, *N. meningitidis* or *spirochaeta*, and preferably, may be BL21 (DE3). BL21 (DE3) is referred also as BL21 below. Bacteria are classified into Gram-positive bacteria and Gram-negative bacteria based on the components of a cell wall.

The Gram-positive bacteria have peptidoglycan and LTA. The Gram-negative bacteria contain LPS in the cell wall, and the peptidoglymay between the cell wall and the cell membrane. Thus, the LTA antigen may include all antigens, bacteria, cells, proteins, organic compounds, or inorganic compounds including LTA. The LPS antigens may include all antigens, bacteria, cells, proteins, organic compounds or inorganic compounds including LTA, and the antigens are not limited to the above examples.

Figure 2:
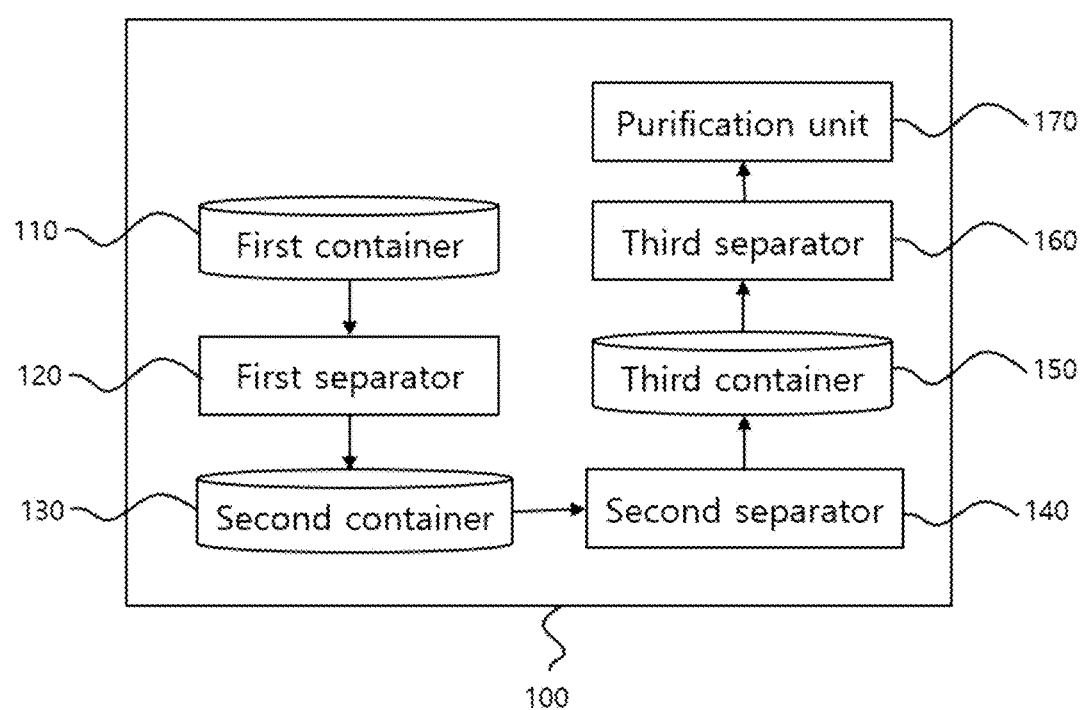
FIG. 2 is a block diagram showing the configuration of an antibody screening system according to an embodiment of the present invention, where the reference numeral 100 denotes the antibody screening system, 110 denotes a first container, 120 denotes a first separator, 130 denotes a second container, 140 denotes a second separator, 150 denotes a third container, 160 denotes a third separator, and 170 denotes a purification unit.

FIG. 2 is a block diagram showing the configuration of the antibody screening system 100 according to an embodiment of the present invention.

Referring to FIG. 2, the antibody screening system 100 according to an embodiment includes a first container 110, a first separator 120, a second container 130, a second separator 140, and a third container 150 and a third separator 160, and the antibody screening system 100 according to another embodiment may further include a purification unit 170. The components of the antibody screening system 100 may be interconnected with flow paths for mass transfer for a continuous process, and valves for flow control may be coupled to these flow paths. The components may be entirely automated systems, and at least some of which may be combinations of manually driven equipment, control devices or experimental steps. The arrows may be indicative of the order in which the target mixture or solutions are processed. In various embodiments, the components may be individualized systems, at least some of the components may be merged, and some of the components may be omitted. In addition, the description of each component of the antibody screening system 100 refers to the foregoing disclosure in FIG. 1 to avoid duplication if there are no discrepancies.

In one embodiment, the containers may be at least any one or more of a well, a cell, a substrate, a cell pellet or a plate provided with a reaction zone. In other embodiments, the containers may include laboratory tools, laboratory equipment for solution processing, such as the provision, addition, or solution treatment of the solution, and the solution process may be performed automatically by the antibody screening system 100, or may be performed by a person.

In one embodiment, the separators may use a process using manure, distillation, and density difference, centrifuge, spinning band extraction, Pulsating Sieve Tray or Packed Columns Extraction Systems or liquid mixer-settler. However, this is exemplary and all methods capable of separating liquid-liquid, liquid-solid or solid-solid may be applicable, and are not limited to specific methods. In another embodiment, the solvent of the solution to be separated may be removed, and then the substances to be separated may be obtained in a solvent-free solid state and then separated.

In one embodiment, the first container 110 prepares a serum SR having a target antibody TAB and a non-target antibody NTAB from a subject and provides the serum SR with a first antigen AG1 that specifically binds to a target antibody TAB. Therefore, the first mixture MX1 comprising the target antibody TAB, the first antigen AG1 of the first conjugate BND1, and the non-target antibody NTAB may be obtained. Serum SR may be extracted from a subject and provided to the antibody screening system 100, and the antibody screening system 100 may collect serum from the subject. In another embodiment, the first container 110 may provide an environment for an immune response based on the first antigen AG1 of serum SR to produce a target antibody TAB and a non-target antibody NTAB.

In another embodiment, the first container 110 may automatically adjust the optimum amount by detecting the amount of a target antibody TAB, a non-target antibody NTAB or a binder BND1 within the first mixture MX1 while increasing the dose of the first antigen AG1 starting at 0 ml.

For example, the substances in the first mixture MX1 are labeled to be detected by using optical, electrical or chemical reactions, and an optimal injection dosage of the first antigen AG1 is injected until all of the target antibody TAB forms the first conjugate BND1.

In one embodiment, the first separator 120 may selectively obtain the first conjugate BND1 by separating the first conjugate BND1 and the non-target antibody NTAB from the first mixture MX1. The second container 130 may be configured to dissociate the first conjugate BND1, and the redundant non-target antibody RDAB adsorbed onto the first conjugate BND1 into the first antigen AG1, the target antibody TAB, and the redundant non-target antibody RDAB. The second separator 140 may remove the first antigen AG1 to obtain a second mixture MX2 of the target antibody TAB and the redundant non-target antibody RDAB. In addition, the third container 150 provides a second antigen AG2 that specifically binds the redundant non-target antibody RDAB to the first mixture MX1, so that the second binder BND2 consisting of the redundant non-target antibody RDAB and the second antigen AG2 may be formed. Therefore, a third mixture MX3 comprising the target antibody TAB and the second antigen AG2 may be obtained. In another embodiment, the injection amount of the second antigen AG2 may be automatically adjusted, and the above disclosure related to the first container 110 may be referred to.

In one embodiment, the third separator 160 may selectively obtain the target antibody TAB by separating the second conjugate BND2 and the target antibody TAB from a third mixture MX3. In another embodiment, the antibody screening system 100 may further include a purification unit 170 for purifying the target antibody TAB from the mixed solution from which the second conjugate BND2 has been removed. For example, at least one or more methods of ion exchange chromatography, hydrophobic interaction chromatography (HIC), protein-G chromatography, or protein-A chromatography may be used.

Figure 3A:
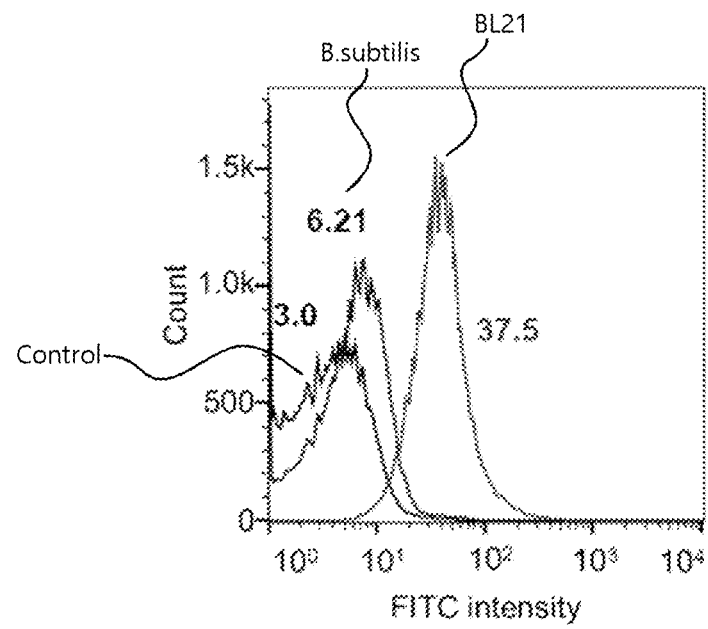
FIG. 3A illustrates a result of fluorescence-activated cell sorting (FACS) analysis of binding Gram-positive bacteria to LTA antibodies selected according to one embodiment.
Figure 3B:
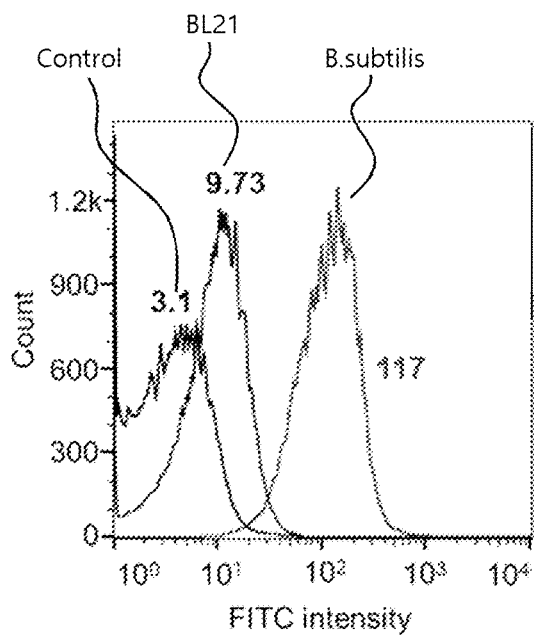
FIG. 3B illustrates FACS result of binding Gram-negative bacteria to LPS antibodies selected according to one embodiment, and in FIGS. 3A and 3B, *B. subtilis* corresponds to the Gram-positive bacteria and BL21 denotes an *Escherichia coli* (*E. coli*) which corresponds to the Gram-negative bacteria.

FIG. 3A is a result of fluorescence-activated cell sorting (FACS) analysis of binding of Gram-positive bacteria and LTA antibodies selected according to one embodiment, and FIG. 3B illustrates FACS results of binding of Gram-negative bacteria and LPS antibodies selected according to one embodiment. FACS results.

In one embodiment, the Gram-positive bacteria may be *B. subtilis* and the Gram-negative bacteria may be BL21. The FITC intensity on the x-axis of the graph represents the intensity of fluorescence measured by FACS, and it means that as the intensity of fluorescence is getting higher and higher, the binding strength becomes stronger. However, the substances of one embodiment are merely examples and may be equally applied to all kinds of Gram-positive bacteria or Gram-negative bacteria. Referring to FIG. 3A, in the case of the LTA antibody, it may be observed that the fluorescence intensity of BL21 has the largest value, 37.5 because LTA is included in the cell wall of BL21, a Gram-negative bacterium. Referring to FIG. 3B, it may be seen that the fluorescence intensity of *B. subtilis* is the largest in the case of LPS antibody, 117 because LPS is included in the cell wall of *B. subtilis*, a Gram-negative bacterium.

In one embodiment, the Gram-positive bacteria may be *B. subtilis* and the Gram-negative bacteria may be BL21. The FITC intensity on the x-axis of the graph represents the intensity of fluorescence measured by FACS, and the greater the intensity of fluorescence, the stronger the binding. However, the materials of one embodiment are merely examples and may be equally applied to all kinds of Gram-positive bacteria or Gram-negative bacteria. Referring to FIG. 3A, in the case of the LTA antibody, the fluorescence intensity of BL21 is shown to be the largest at 37.5, because LTA is included in the cell wall of BL21, a Gram-negative bacterium. Referring to FIG. 3B, it may be seen that the fluorescence intensity of *B. subtilis* is the largest in the case of LPS antibody, 117, because LPS is included in the cell wall of *B. subtilis*, a Gram-positive bacterium.

Figure 4A:
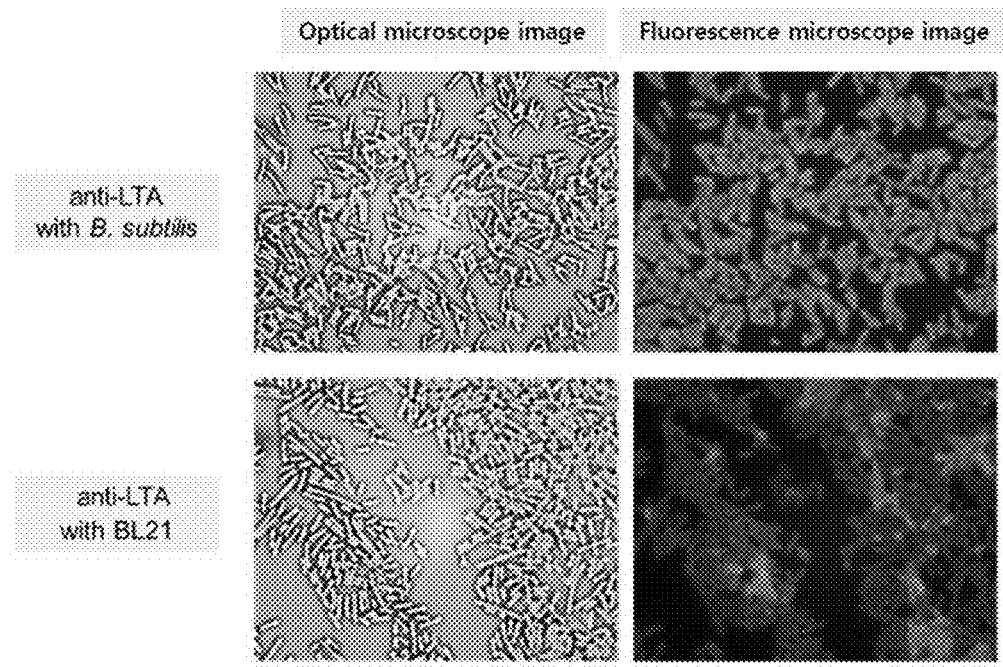
FIG. 4A is an image which was taken with a fluorescence microscope when a LTA antibody selected according to one embodiment is reacted with Gram-positive bacteria and Gram-negative bacteria.
Figure 4B:
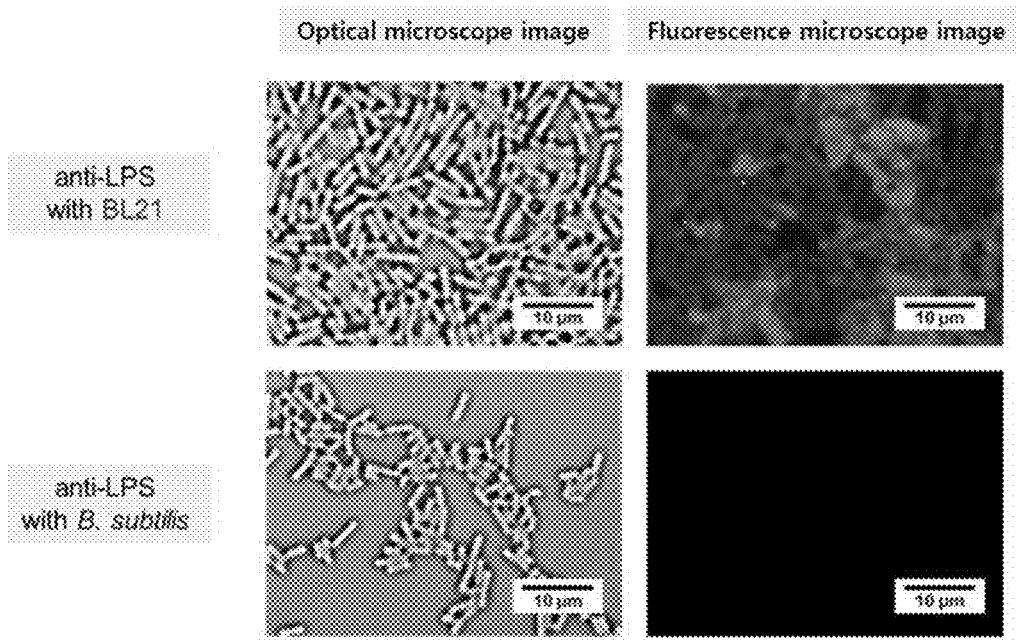
FIG. 4B is an image which was taken under a fluorescence microscope when LPS antibodies selected according to one embodiment is reacted with Gram-positive bacteria and Gram-negative bacteria.

FIG. 4A is an image which was taken with a fluorescence microscope after performing a step for reacting LTA antibody selected according to one embodiment of the present invention with Gram-positive bacteria and Gram-negative bacteria. FIG. 4B is an image which was taken with a fluorescence microscope after performing a step for reacting LPS antibody selected according to one embodiment of the present invention with Gram-positive bacteria and Gram-negative bacteria.

As described above, the Gram-positive bacteria may be *B. subtilis*, and the Gram-negative bacteria may be BL21, which are only illustrative and they do not limit the present invention. Referring to FIG. 3A, the LTA antibody selected according to one embodiment binds strongly to *B. subtilis* and shows high fluorescence intensity. The reason of this is that *B. subtilis* is a Gram-positive bacterium having LTA on the cell wall. Referring to FIG. 3B, the LPS antibody selected according to the embodiment binds strongly with BL21 and exhibits high fluorescence intensity. The reason of this is that *B. subtilis* is a Gram-positive bacterium having LPS on the cell wall. Further, referring to FIGS. 4A and 4B, it may be observed that the LTA antibody partially reacts with Gram-negative bacteria having LPS, and vice versa. This means that it is difficult to obtain an LPS antibody or an LTA antibody having a high selection rate according to an anti-selection process based on any one type of LPS antigen or LTS antigen. In the antibody screening method according to the present invention, high-quality antibodies may be obtained by performing antibody screening using 2-track based on LPS antigen and LTA antigen.

Figure 5A:
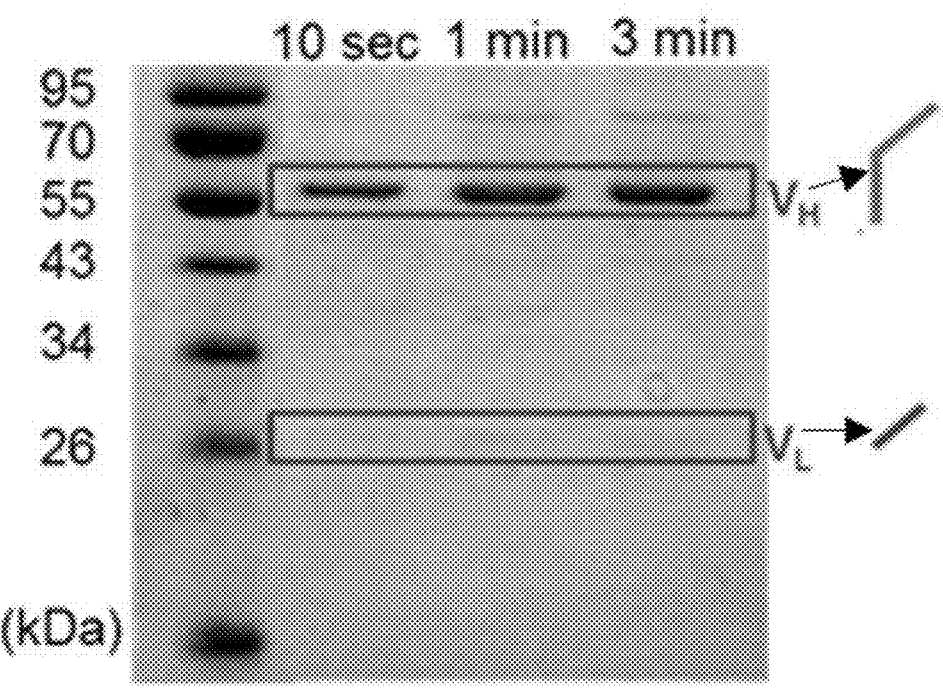
FIG. 5A is a result of sodium dodecyl sulfate-polyacrylamide gel electrophoresis (SDS-PAGE) of LTA antibodies selected according to one embodiment.
Figure 5B:
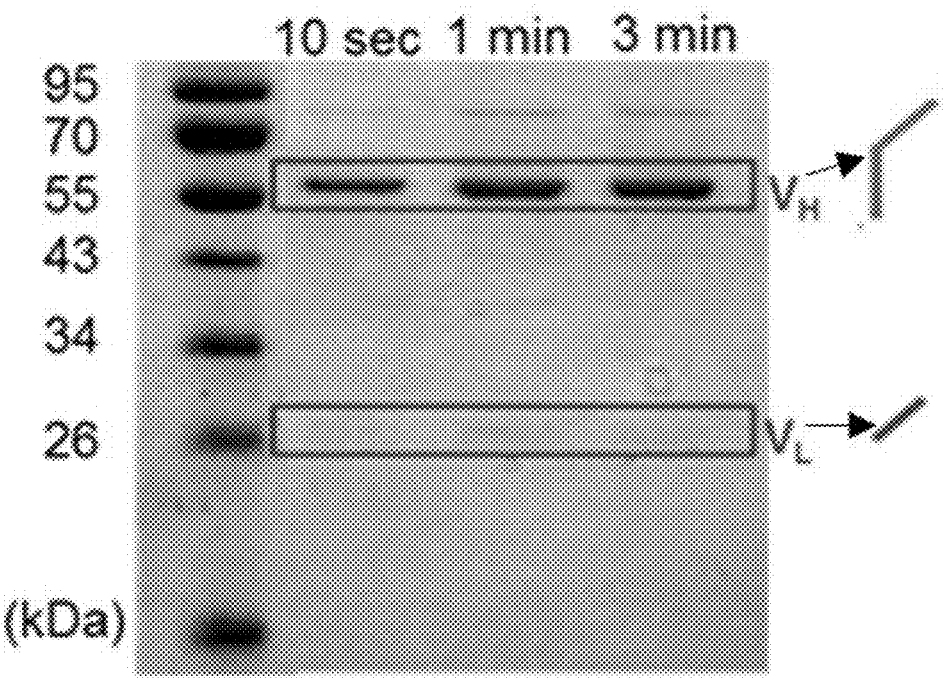
FIG. 5B is SDS-PAGE results of LPS antibodies selected according to another embodiment.

FIG. 5A shows a result of sodium dodecyl sulfate-polyacrylamide gel electrophoresis (SDS-PAGE) of LTA antibodies selected according to one embodiment, and FIG. 5B shows SDS-PAGE results of LPS antibodies selected according to another embodiment.

Referring to FIG. 5A, in one embodiment of the present invention, the target antibody TAB may be an LTA antibody, the non-target antibody NTAB may be an LPS antibody, the first antigen AG1 may be an LTA antigen, and the second antigen AG2 may be an LPS antigen. Referring to FIG. 5B, in another embodiment, the target antibody TAB may be an LPS antibody, the non-target antibody NTAB may be an LTA antibody, and the first antigen AG1 may be a PS antigen and the second antigen AG2 may be an LTA antigen. In another embodiment, in the dissociation step (S400) of the first conjugate BND1, the first conjugate BND1 may be dissociated when an acid solution is provided, and the acid solution may be Glycine-HCl buffer pH 2.7, 0.1M. In various embodiments, the acid solution may be treated for 10 seconds, 1 minute, or 3 minutes, and the treatment time of the acid solution is exemplary and is not limited to the above values. The y-axis of FIGS. 5A and 5B refers to the molecular weight (kDa) of protein molecules separated by SDS-PAGE, the numbers on the top means the treatment time of the acid solution.

In the SDS-PAGE results of the present invention, VH means long protein chain of 55 kDa molecular weight and VL means short protein chain of 26 kDa molecular weight. Accordingly, in one embodiment, it may be seen that the two types of target antibody TAB of the long protein chain or short protein chain is selected in connection with the target antibody TAB selected by the antibody screening method or the antibody screening system 100. In another embodiment, the protein chain of the target antibody TAB may be three or more types.

In another embodiment, the antibody screening method may further comprise a step for classifying the selected target antibody TAB according to the length or molecular weight of the protein chain, and the antibody screening system 100 further may include an antibody classification unit for classifying the protein chain. In one embodiment, the target antibody TAB may be classified by using at least one or more of a moving boundary electrophoresis, a zone electrophoresis, disc electrophoresis, SDS-PAGE, isoelectric focusing or isothermal isochophoresis (ITP). All methods that may classify proteins according to molecular weight may be used, and are not limited to the examples described above. By classifying the target antibody TAB according to the types of the protein chains, high-quality antibody production may be possible.

In another embodiment, the treatment time of the acid solution in the step S400 for dissociating the first conjugate BND1 may be set within the range of 30 seconds to 1 minute. In the SDS-PAGE results, it may be seen that the amount of target antibody TAB was much higher in a case that the treatment time of the acid solution was greater than 1 minute than that of the target antibody TAB when the treatment time of the acid solution was 10 seconds. When the treatment time of the acid solution is 1 minute min or more, it may be seen that the amount of target antibody TAB is constant even if the treatment time is longer. When the processing time is less than 30 seconds, sufficient dissociation was not executed in the step S400 for dissociating the first conjugate BND1. Therefore, in step S500 for removing the first antigen AG1 to obtain the second mixture MX2, since a portion of the target antibody TAB bound to the first antigen AG1 is removed together with the first antigen AG1, the yield of antibody screening may be reduced. In addition, by setting the treatment time within 1 minute, the time required for antibody selection may be shortened while maintaining a high yield of antibody selection.

In one embodiment, the assay for quantifying the target antibody TAB selected by the antibody screening method and antibody screening system 100 may be further performed. For example, it may be quantified by bicinchoninate (BCA), EIA assay, RIA assay, fluorescence antibody method or western blotting. Further, a quantitative analysis of the target antibody TAB was performed to measure the yield and screening rate of the selected target antibody TAB in various examples, so that volume ratio, and concentration of the solution and experimental conditions may be set for commercialization during the selection process using various kinds of antibodies or antigens.

It will be apparent to those having a common knowledge in the related art to which the present invention belongs that the present invention described above is not limited to the above-described embodiments and the accompanying drawings, and various substitutions, modifications, and changes are possible within the scope without departing from the technological concepts of the present invention.

EXPLANATION OF DENOTATION

SR: serum
TAB: target antibody
NTAB: non-target antibody
AG1: first antigen
AG2: second antigen
BND1: first conjugate
BND2: second conjugate
MX1: first mixture
MX2: second mixture
MX3: third mixture
RDAB: redundant non-target antibody
100: antibody screening system
110: first container
120: first separator
130: second container
140: second separator
150: third container
160: third separator
170: purification unit

What is claimed is:
1. A method of screening an antibody comprising:
preparing a serum including a target antibody and a non-target antibody from a subject, wherein the preparing of the serum comprises extracting the subject's serum from the subject for the serum and providing a container containing the serum;
providing the serum with a first antigen that specifically binds the target antibody to obtain a first mixture including a first conjugate and the non-target antibody, the first conjugate comprising the target antibody and the first antigen, wherein, in the first conjugate, the target antibody is bound to the first antigen, so that the first conjugate comprises the target antibody bound to the first antigen;

selectively obtaining the first conjugate by separating the first conjugate from the non-target antibody in the first mixture, wherein by centrifuging the first mixture to precipitate the first conjugate or leaving the first mixture to precipitate the first conjugate by gravity, and then extracting the precipitated first conjugate or removing a first solution including the nontarget antibody existing on the precipitated first conjugate, the first conjugate and the nontarget antibody are separated from the first mixture;

dissociating the first conjugate and a redundant non-target antibody adsorbed to the first conjugate into the first antigen, the target antibody and the redundant non-target antibody;

removing the first antigen to obtain a second mixture of the target antibody and the redundant non-target antibody, the second mixture including the target antibody and the redundant non-target antibody;

providing the second mixture with a second antigen that specifically binds the redundant non-target antibody to form a second conjugate consisting of the redundant non-target antibody and the second antigen bound to the non-target antibody, so that a third mixture including the target antibody and the second conjugate is obtained; and selectively obtaining a target antibody by separating the second conjugate from the target antibody in the third mixture, wherein by centrifuging the third mixture to precipitate the second conjugate or leaving the third mixture to precipitate the second conjugate by gravity, and then extracting the precipitated second conjugate or removing a second solution including the target antibody existing on the precipitated second conjugate, the second conjugate and the target antibody are separated from the third mixture.

2. The method of claim 1, wherein a concentration of the first antigen in the step of obtaining the first mixture is in the range of $10^6$ cells/ml to $10^8$ cells/ml.

3. The method of claim 1, wherein a concentration of the second antigen in the step of obtaining the third mixture is in the range of $10^6$ cells/ml to $10^8$ cells/ml.

4. The method of claim 1, wherein when the first antigen (AG1) is a lipoteichoic acid (LTA) antigen including LTA in at least some portions of the AG1, the second antigen (AG2) is a lipopolysaccharide (LPS) antigen including LPS in at least some portions of the AG2, or when the AG1 is an LPS antigen including LPS in at least some portions of the AG1, the AG2 is an LTA antigen including LTA in at least some portions of the AG2.

5. The method of claim 4, wherein the LTA antigen comprises Gram positive bacteria.

6. The method of claim 4, wherein the LPS antigen comprises Gram negative bacteria.

7. The method of claim 4, wherein the LTA antigen includes at least any one or more of *streptococcus*, pneumococcus, leprosy, *M. leprae, C. diphtheriae, C. tetani, B. anthracis*, actinobacteria, or *B. subtilis*.

8. The method of claim 4, wherein the LPS antigen includes at least any one or more of *Klebsiella* penumoniae, *Acinetobacter baumannii, Pseudomonas aeruginosa, Enterobacter* spp., *Salmonella, Shigella, R. rickettsii, E. coli, V. cholerae, Y. pestis, N. gonorrhoeae, N. meningitidis*, or *Spirochaeta*.

9. The method of claim 1, wherein the step of obtaining the first mixture further comprises a step for providing the first antigen to the serum to generate the target antibody and the non-target antibody through an immune response of the first antigen.

10. The method of claim 1, wherein the first conjugate is dissociated into the first antigen and the target antibody when an acid solution is provided.

* * * * *